(12) United States Patent
Hooper et al.

(10) Patent No.: US 9,277,946 B2
(45) Date of Patent: Mar. 8, 2016

(54) SPINAL FUSION SYSTEM

(75) Inventors: Bruce Hooper, Waleska, GA (US); Jeff Radcliffe, Marietta, GA (US)

(73) Assignee: Amendia, Inc., Marietta, GA (US)

( * ) Notice: Subject to any disclaimer, the term of this patent is extended or adjusted under 35 U.S.C. 154(b) by 702 days.

(21) Appl. No.: 13/225,708

(22) Filed: Sep. 6, 2011

(65) Prior Publication Data

US 2013/0060336 A1 Mar. 7, 2013

(51) Int. Cl.
*A61F 2/44* (2006.01)
*A61B 17/80* (2006.01)
*A61F 2/30* (2006.01)

(52) U.S. Cl.
CPC ............. *A61B 17/8047* (2013.01); *A61F 2/447* (2013.01); *A61F 2002/30014* (2013.01); *A61F 2002/3036* (2013.01); *A61F 2002/3038* (2013.01); *A61F 2002/30355* (2013.01); *A61F 2002/30492* (2013.01); *A61F 2002/30563* (2013.01); *A61F 2002/30604* (2013.01); *A61F 2002/30787* (2013.01); *A61F 2002/30848* (2013.01); *A61F 2002/30884* (2013.01); *A61F 2002/30904* (2013.01); *A61F 2002/4475* (2013.01); *A61F 2310/00023* (2013.01)

(58) Field of Classification Search
CPC ......... A61F 2/44; A61F 2/442; A61F 2/4455; A61F 2002/443; F16B 41/002
USPC ........ 623/17.11–17.16; 606/70–71, 280–299; 411/315–316, 301–302, 999
See application file for complete search history.

(56) References Cited

U.S. PATENT DOCUMENTS

| | | |
|---|---|---|
| 5,397,364 A | 3/1995 | Kozak et al. |
| 5,578,034 A | 11/1996 | Estes |
| 5,601,553 A | 2/1997 | Trebing et al. |
| 5,683,464 A | 11/1997 | Wagner et al. |
| 5,954,722 A | 9/1999 | Bono |
| 6,235,059 B1 | 5/2001 | Benezech et al. |
| 6,432,106 B1 | 8/2002 | Fraser |
| 6,461,359 B1 | 10/2002 | Tribus et al. |
| 6,579,290 B1 | 6/2003 | Hardcastle et al. |
| 6,740,088 B1 | 5/2004 | Kozack et al. |
| 7,112,222 B2 | 9/2006 | Fraser et al. |
| 7,232,464 B2 | 6/2007 | Mathieu et al. |
| 7,238,203 B2 | 7/2007 | Bagga et al. |
| 7,250,060 B2 | 7/2007 | Trieu |
| 7,468,069 B2 | 12/2008 | Baynham et al. |
| 7,588,590 B2 | 9/2009 | Chervitz et al. |
| 7,780,666 B1 | 8/2010 | Navarro et al. |
| 7,794,502 B2 | 9/2010 | Michelson |

(Continued)

FOREIGN PATENT DOCUMENTS

WO WO 2009/064644 * 5/2009 ............... A61F 2/44

*Primary Examiner* — Anu Ramana
*Assistant Examiner* — Jessica Weiss
(74) *Attorney, Agent, or Firm* — David L. King (57) ABSTRACT

A spinal fusion system for positioning between two vertebral bodies is presented. The system can have a substantially rigid body and a substantially rigid plate connected to a portion of the posterior face of the substantially rigid body that extends away from and substantially transverse to the posterior face of the substantially rigid body. The system also has a first implant body and a second implant body configured to matingly connect to one another with at least a portion of the substantially rigid plate positioned therebetween. The combination of the first and second implant bodies and the substantially rigid plate is configured for insertion between the two vertebral bodies.

21 Claims, 10 Drawing Sheets

(56) References Cited

U.S. PATENT DOCUMENTS

| | | | |
|---|---|---|---|
| 8,043,380 B1 * | 10/2011 | Park et al. | 623/17.16 |
| 2004/0092929 A1 | 5/2004 | Zindrick | |
| 2004/0199253 A1 | 10/2004 | Link et al. | |
| 2006/0100626 A1 | 5/2006 | Rathbun et al. | |
| 2006/0229729 A1 | 10/2006 | Gordon et al. | |
| 2007/0027546 A1 | 2/2007 | Palm et al. | |
| 2008/0183292 A1 | 7/2008 | Trieu | |
| 2008/0269806 A1 | 10/2008 | Zhang et al. | |
| 2008/0294260 A1 * | 11/2008 | Gray | 623/17.16 |
| 2008/0306596 A1 | 12/2008 | Jones et al. | |
| 2009/0024170 A1 | 1/2009 | Kirschman | |
| 2009/0048677 A1 | 2/2009 | McLeod et al. | |
| 2009/0182430 A1 | 7/2009 | Tyber et al. | |
| 2009/0192553 A1 * | 7/2009 | Maguire et al. | 606/305 |
| 2009/0276051 A1 | 11/2009 | Arramon et al. | |
| 2010/0016970 A1 * | 1/2010 | Kapitan et al. | 623/17.12 |
| 2010/0042216 A1 | 2/2010 | Kilpela et al. | |
| 2010/0057204 A1 | 3/2010 | Kadaba et al. | |
| 2010/0312346 A1 | 12/2010 | Kueenzi et al. | |

* cited by examiner

SPINAL FUSION SYSTEM

FIELD OF THE INVENTION

Presented herein is a spinal fusion system. More specifically, a spinal fusion system for interbody implantation or corpectomy implantation in spine surgery.

BACKGROUND OF THE INVENTION

There are several procedures available to patients with degenerative spine conditions. For example, Anterior Lumbar Interbody Fusion ("ALIF") has been performed by surgeons since the 1950's. In an ALIF procedure, the disc space is fused by approaching the spine through the abdomen. In the ALIF approach, a three-inch to five-inch incision is made on the left side of the abdomen and the abdominal muscles are retracted to the side. Since the anterior abdominal muscle in the midline (rectus abdominis) runs vertically, it does not need to be cut and easily retracts to the side. The abdominal contents lay inside a large sack (peritoneum) that can also be retracted, thus allowing the spine surgeon access to the front of the spine without actually entering the abdomen. There is also a less popular transperitoneal approach that accesses the spine through the abdomen. This adds a lot of unnecessary morbidity to the procedure and therefore is used much less often.

Another technique is called Posterior Lumbar Interbody Fusion ("PLIF"). In the PLIF approach, the spine is accessed through a three-inch to six-inch long incision in the midline of the back and the left and right lower back muscles are stripped off the lamina on both sides and at multiple levels. After the spine is approached, the lamina is removed, which allows visualization of the nerve roots. The facet joints, which are directly over the nerve roots, may then be undercut to give the nerve roots more room. The nerve roots are then retracted to one side and the disc space is cleaned of the disc material. A bone graft, or an interbody cage, is then inserted into the disc space and the bone grows from vertebral body to vertebral body.

Still another procedure is a Transforaminal Lumbar Interbody Fusion ("TLIF"). By removing the entire facet joint, visualization into the disc space is improved and more disc material can be removed. It should also provide for less nerve retraction. Because one entire facet is removed, it is only done on one side. Removing the facet joints on both sides of the spine would result in too much instability. With increased visualization and room for dissection, a larger implant and/or bone graft can be used. Although this has some improvements over a PLIF procedure, the anterior approach, in most cases still provides the best visualization, most surface area for healing, and the best reduction of any of the approaches to the disc space.

There are other approaches know in the art, as well. For instance, Direct Lateral Interbody Fusion, Axial Lift using a transsacral approach, and the like. Additionally, there are similarly pluralities of methods for correcting degenerative issues with the cervical spine. Those skilled in the art will appreciate that these and other known procedures have benefits, as well as disadvantages. As such, more beneficial approaches in the art are needed.

SUMMARY

Presented herein are systems, methods, and apparatuses for spinal fusion. In one aspect, presented herein is a spinal fusion system for positioning between two vertebral bodies. As such, the system can be used as an interbody system, or as a disc replacement system. In one aspect, the system comprises a substantially rigid body that defines at least one fastener bore therethrough, where each bore is configured for receipt of at least one fastener. In this aspect, each fastener is configured for insertion into one of the two vertebral bodies.

In another aspect, the system comprises a substantially rigid plate connected to a portion of the posterior face of the substantially rigid body that extends away from and substantially transverse to the posterior face of the substantially rigid body. In one aspect, the system has a first implant body and a second implant body. The first and second implant bodies are configured to matingly connect to one another with at least a portion of the substantially rigid plate positioned therebetween. As such, the combination of the first and second implant bodies and the substantially rigid plate is configured for insertion between the two vertebral bodies. In the case of a corpectomy, the combination can be inserted in the space made by the removal of a disc.

Related methods of operation are also provided. Other apparatuses, methods, systems, features, and advantages of the location module will be or become apparent to one with skill in the art upon examination of the following figures and detailed description. It is intended that all such additional apparatuses, methods, systems, features, and advantages be included within this description, be within the scope of the spinal fusion system, and be protected by the accompanying claims.

BRIEF DESCRIPTION OF THE DRAWINGS

These and other features of the preferred embodiments of the present invention will become more apparent in the detailed description in which reference is made to the appended drawings wherein.

DETAILED DESCRIPTION OF THE INVENTION

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein are systems, methods, and apparatuses for spinal fusion. In one aspect, presented herein is a spinal fusion system 10 for positioning between two vertebral bodies, which in most cases are adjacent one another. As such, the system can be used as an interbody system, or as a partial or full disc replacement system. In one aspect, the system comprises a substantially rigid body 100 having a longitudinal axis $A_L$ and a first modulus of elasticity. The substantially rigid body 100 defines at least one fastener bore 110 therethrough, where each bore is configured for receipt of at least one fastener 200. In this aspect, each fastener 200 is configured for insertion into one of the first or second vertebral bodies 15, 17.

In another aspect, the system comprises a substantially rigid plate 300 connected to a portion of the posterior face 120 of the substantially rigid body that extends away from and substantially transverse to the posterior face 120 of the substantially rigid body. In one aspect, the system has a first implant body 400 and a second implant body 410, where each body has a modulus of elasticity less than or equal to the first modulus of elasticity of the substantially rigid plate 300. The first and second implant bodies are configured to matingly connect to one another with at least a portion of the substantially rigid plate positioned therebetween. As such, the combination of the first and second implant bodies and the substantially rigid plate is configured for insertion between the two vertebral bodies. In the case of a corpectomy, the combination can be inserted in the space made by the either partial or full removal of a disc.

The thickness of the first and second implant bodies can vary according to the need of the surgeon and the anatomy of the patient. The thickness of the two bodies can be equal or either one of them can be thicker than the other, depending upon the particular circumstance. Additionally, as one skilled in the art can appreciate, the first implant body 400 can comprise the same material as the second implant body 410. However, it may also differ in composition. In one aspect, the first implant body comprises a thermoplastic material. As such, in another aspect the second implant body can also comprise a thermoplastic material. In yet another aspect, the thermoplastic material can comprise polyetheretherketone.

In one aspect, the substantially rigid plate 300 is substantially bisected by a first plane $P_1$ that contains the longitudinal axis. Yet, in other aspects, the substantially rigid plate can be in a plane that is offset from the longitudinal axis.

Figure 6:
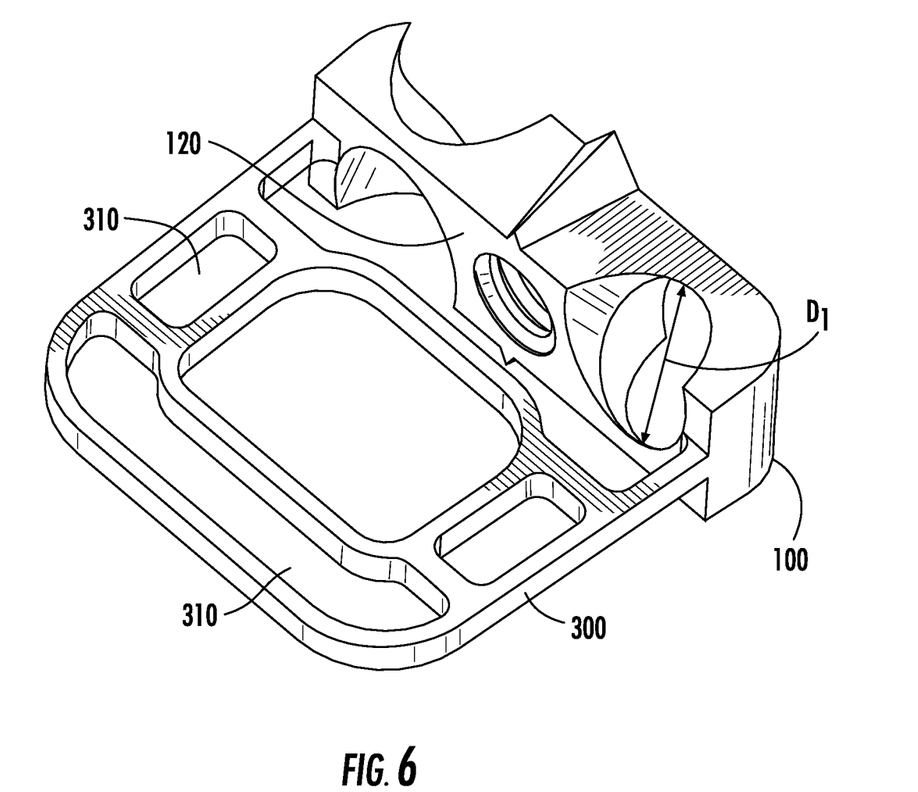
FIG. 6 is a perspective view of one aspect of a rigid body and a rigid plate for use in a spinal fusion system.

Referring now to FIG. 6, in an exemplified aspect, the substantially rigid plate defines at least one cavity 310 therethrough. In this aspect, the first implant body and the second implant body can matingly connect substantially within the at least one cavity 310. As can be appreciated, in another exemplified aspect, the substantially rigid plate 300 defines a plurality of cavities therethrough and the first implant body and the second implant body matingly connect within each of the cavities along their first respective surfaces wherein the first implant body and the second implant body connect at their respective first surfaces, the first surfaces having a plurality of projections, and within each of the cavities are matingly connected at their first respective surfaces by the plurality of projections of the first implant body interlocking with the plurality of projections of the second implant body.

The substantially rigid plate and the substantially rigid body 100 can be connected in various common means. However, in one aspect, the substantially rigid body and the substantially rigid plate are integral.

As mentioned above, the substantially rigid body defines at least one fastener bore 110 therethrough, where each bore is configured for receipt of at least one fastener such that a fastener 200 can be inserted into one of the first or second vertebral bodies. In one aspect, there can be a plurality of fastener bores with corresponding fasteners. In an exemplified aspect, at least one of the fasteners can be angled upwardly with respect to the first plane $P_1$ and another fastener can be angled downwardly with respect to the first plane.

Although, it is contemplated that the fasteners are disposed at various angles, in one aspect, the first and second fasteners are oppositely disposed at substantially equal angles α. In another aspect, the substantially equal angles are between about 20 degrees and about 45 degrees. In still another aspect, the angles are about 35 degrees.

While various materials of construction suitable for implantation into the human body are contemplated, in one aspect, at least one of the substantially rigid plate and the substantially rigid body 100 comprises titanium. In other aspect, both the rigid plate and rigid body comprise titanium.

Figure 7A:
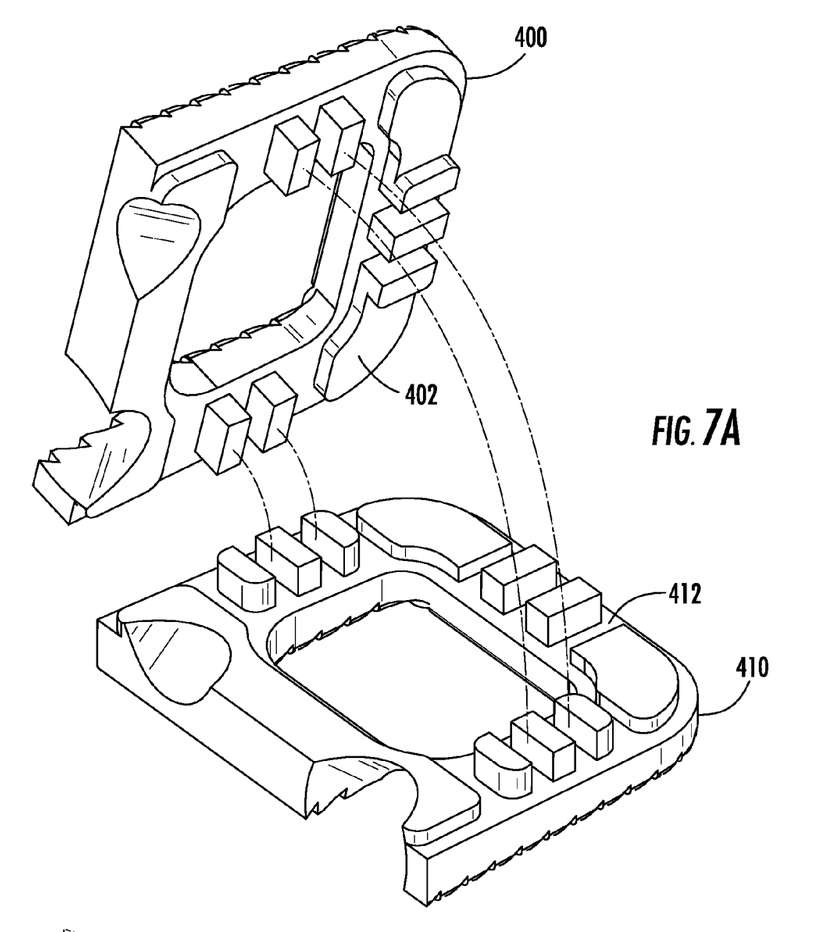
FIG. 7A is a perspective view of one aspect of a pair of implant bodies for use in a spinal fusion system.
Figure 7B:
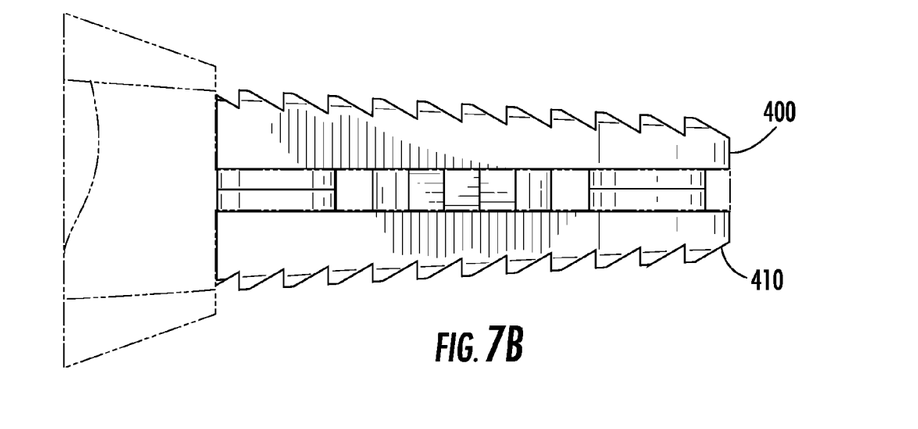
FIG. 7B is a partially transparent side elevational view of the spinal fusion system of FIG. 1, showing a pair of implant bodies connected to one another.
Figure 8:
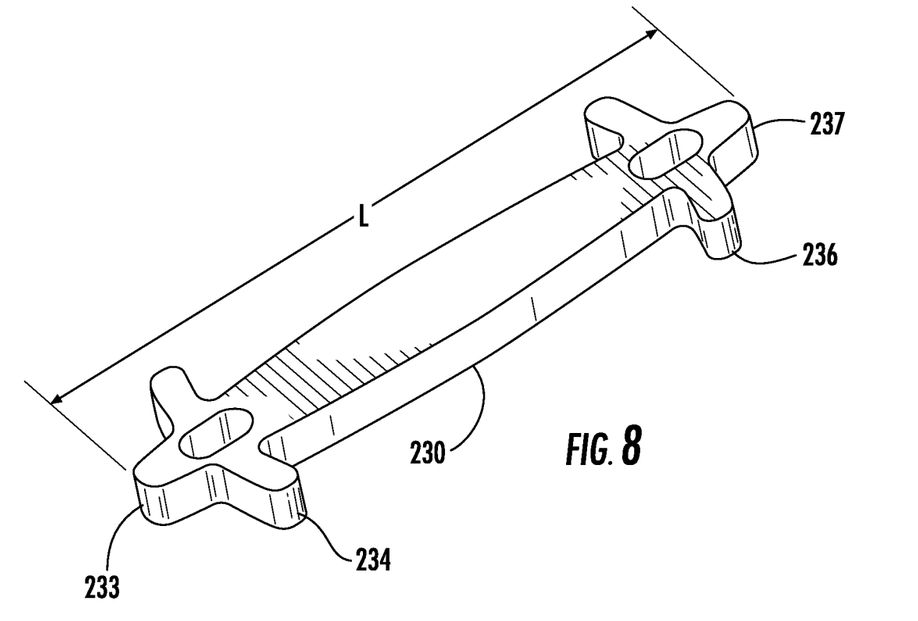
FIG. 8 is a perspective view of one aspect of a retainer pin for use in a spinal fusion system.
Figure 9A:
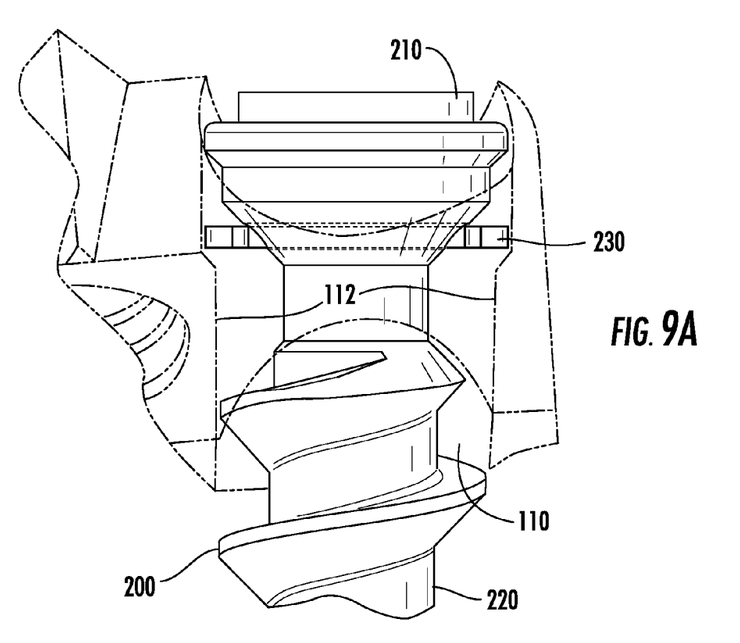
FIG. 9A is a partially transparent side elevational view of one aspect of a fastener with a retaining pin in its original unbiased state.
Figure 9B:
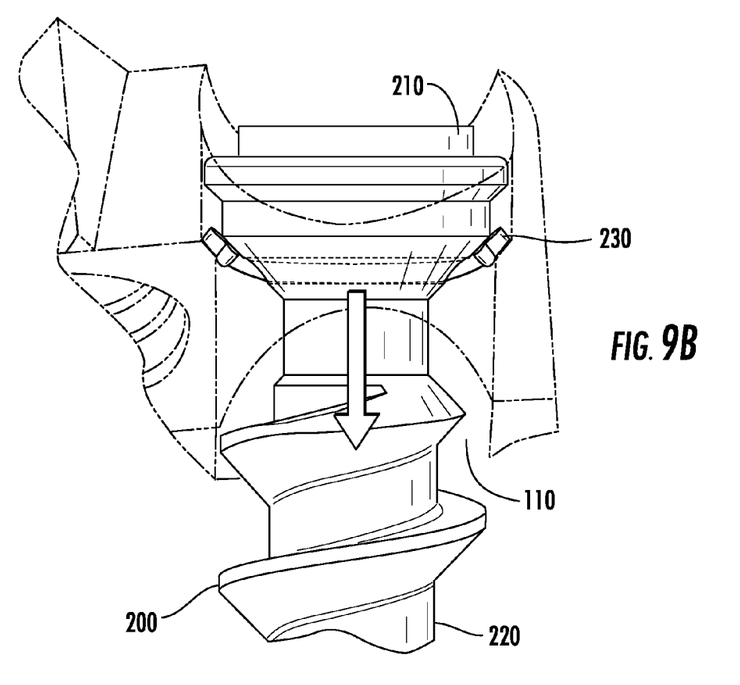
FIG. 9B is a partially transparent side elevational view of the fastener of FIG. 9A with the retaining pin in its biased state.
Figure 10:
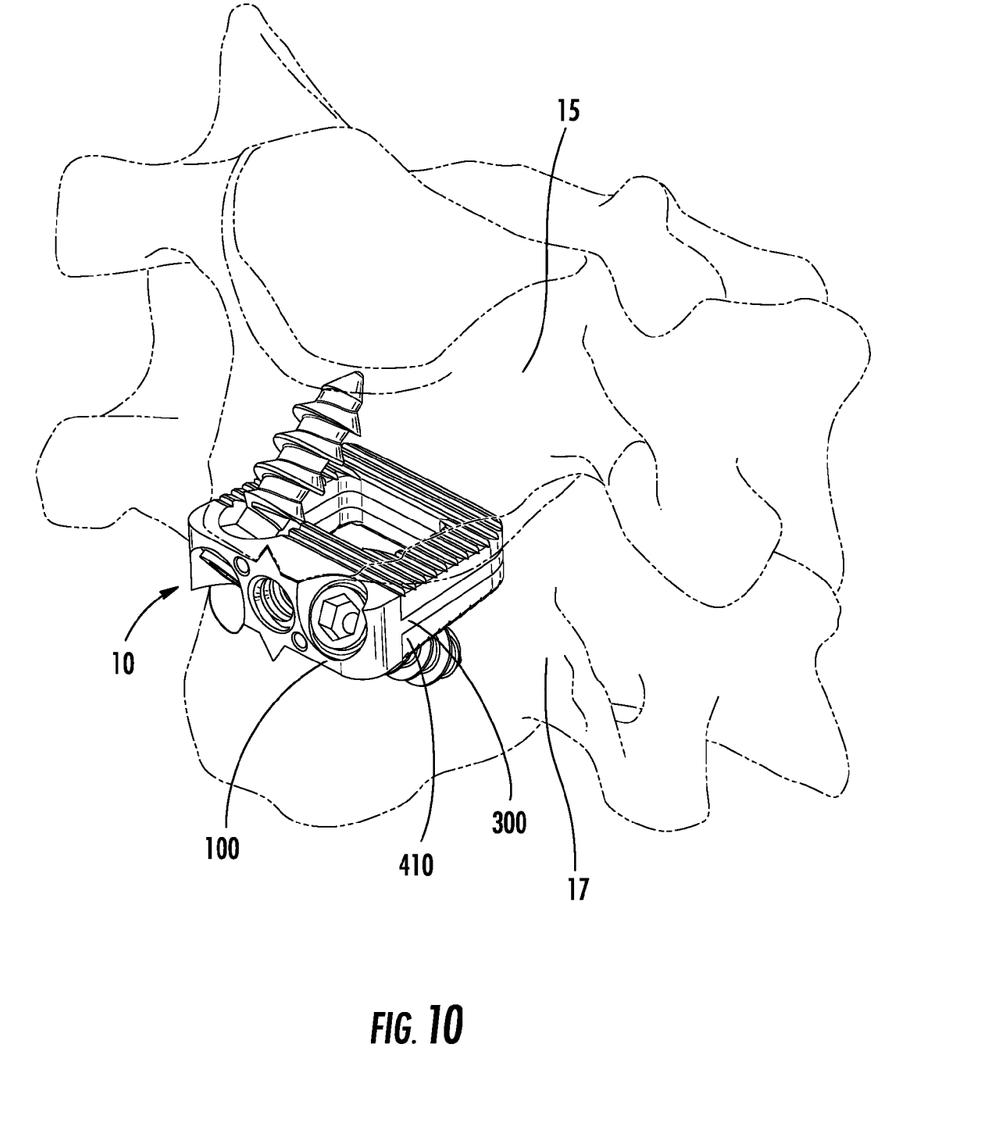
FIG. 10 is a partially transparent perspective view of the spinal fusion system of FIG. 1, shown in position between two vertebral bodies.

As shown in FIG. 7A, the first implant body and the second implant body each have a first and second surface and wherein the first implant body and the second implant body connect at their respective first surfaces 402 412. In one aspect, at least one of the second surfaces 404, 414 of the first implant body and the second implant body are ramped downwardly away from the substantially rigid body. In another aspect, both bodies have second surfaces that are ramped downwardly away from the substantially rigid body. This configuration makes insertion easier.

In yet another exemplified aspect, at least one of the second surfaces of the first implant body and the second implant body define ridges 420. It is also contemplated that both second surfaces define ridges 420 to assist in retaining the system between the two vertebral bodies.

Figure 1:
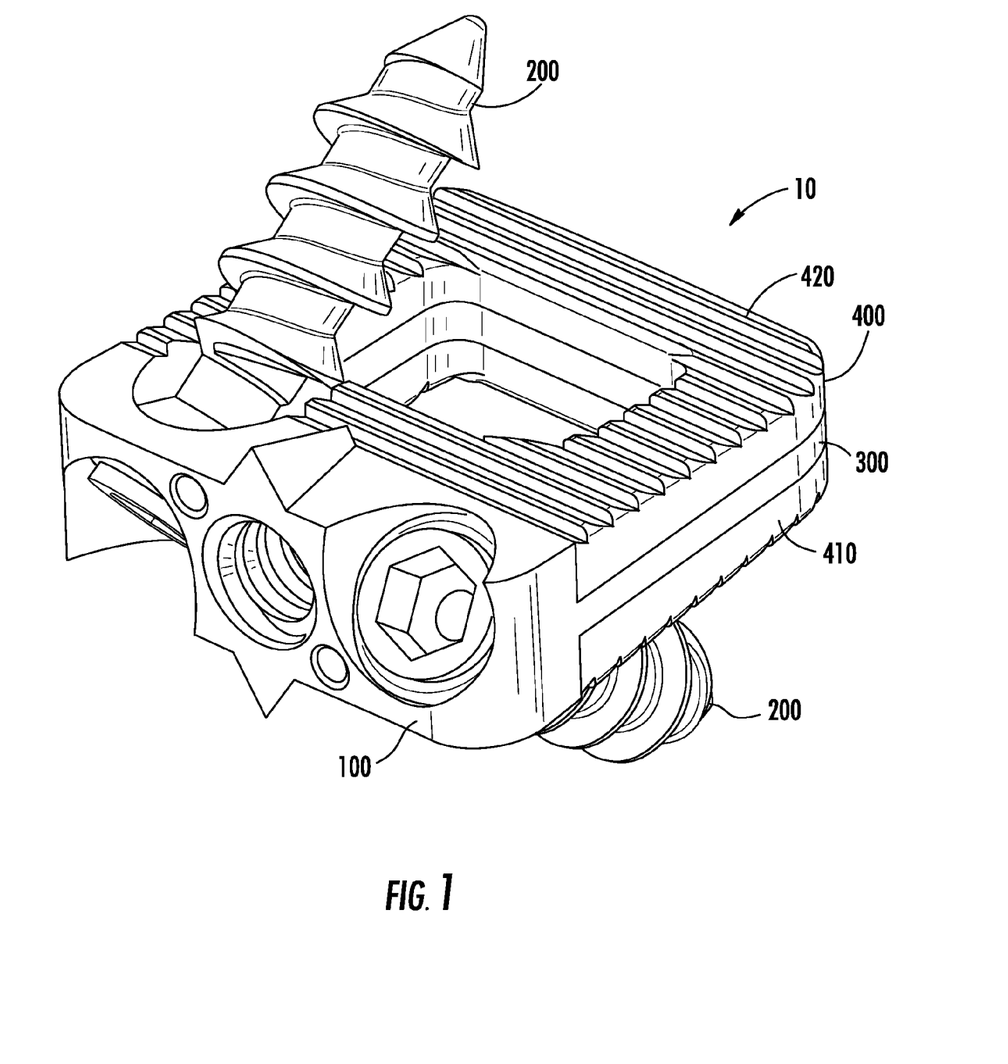
FIG. 1 is a perspective view of one aspect of a spinal fusion system.
Figure 2:
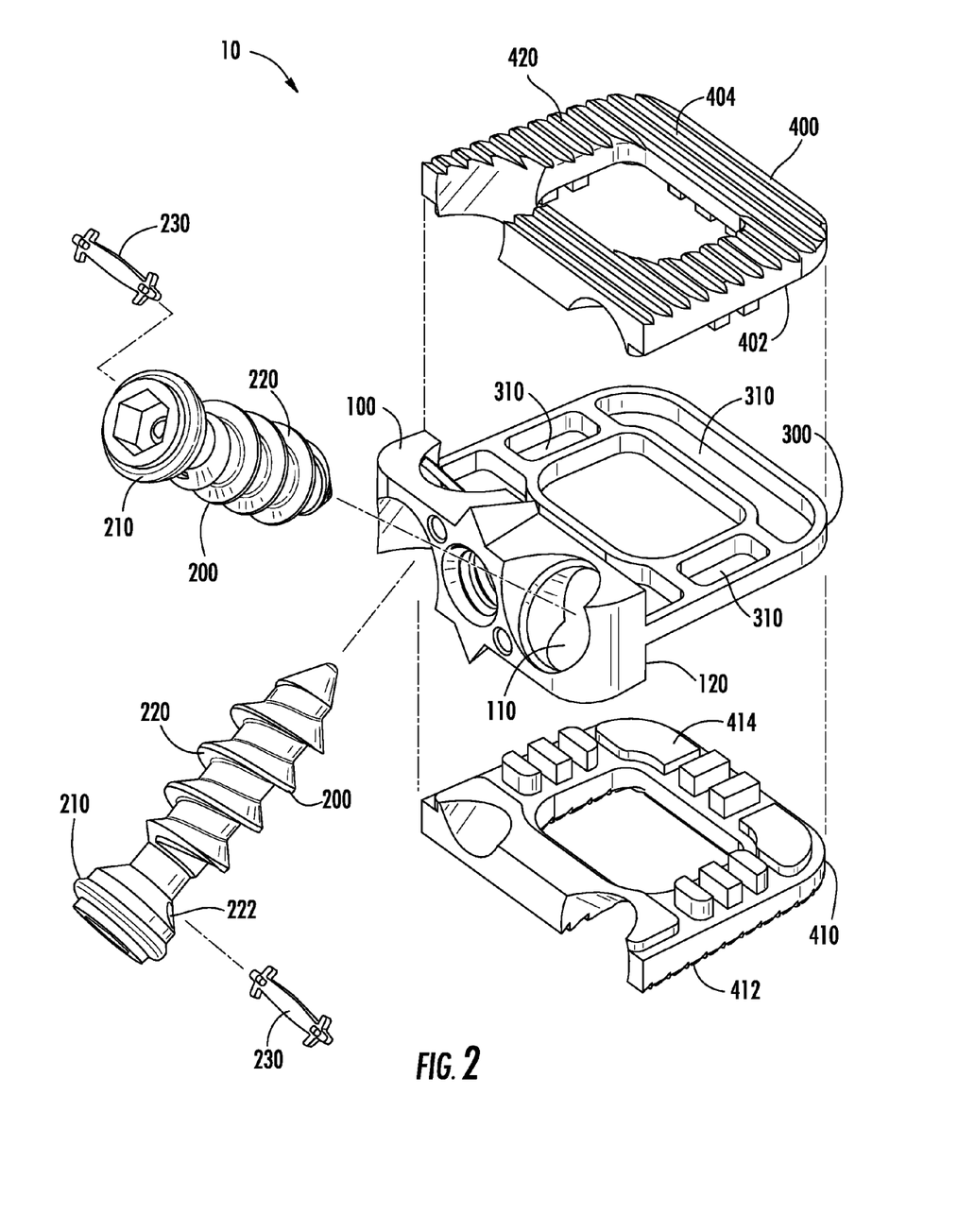
FIG. 2 is an exploded perspective view of one aspect of the spinal fusion system of FIG. 1, showing a rigid body integrally connected to a rigid plate.
Figure 3:
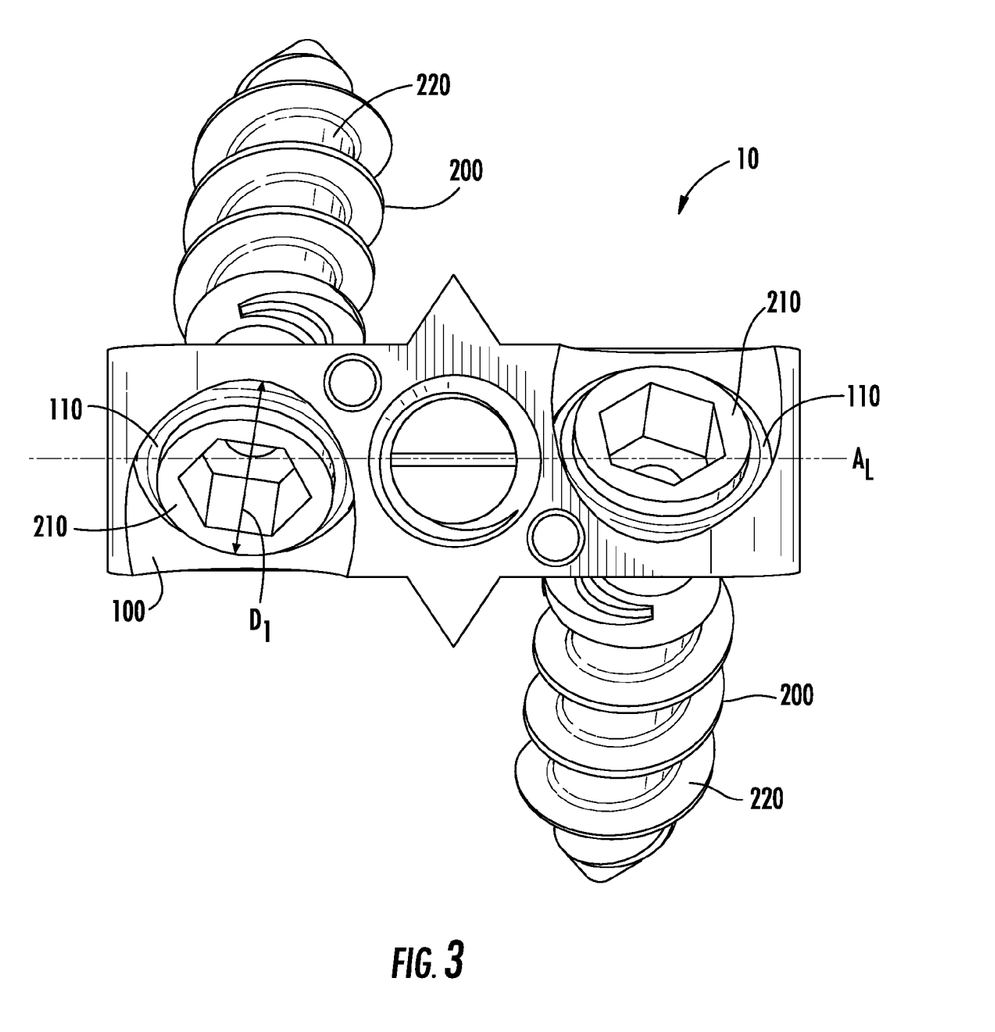
FIG. 3 is a front elevational view of one aspect of the spinal fusion system of FIG. 1.
Figure 4:
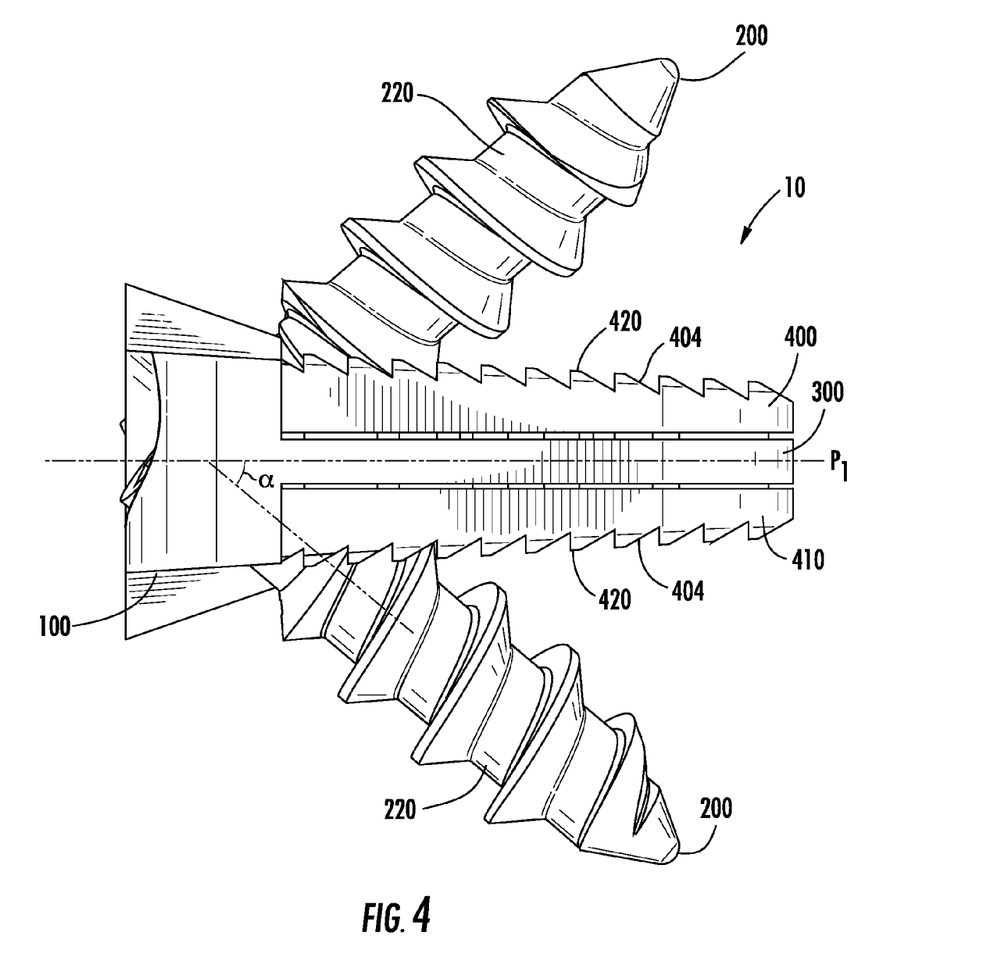
FIG. 4 is a side elevational view of one aspect of the spinal fusion system of FIG. 1, showing the angle α of the fasteners to the first plane.
Figure 5:
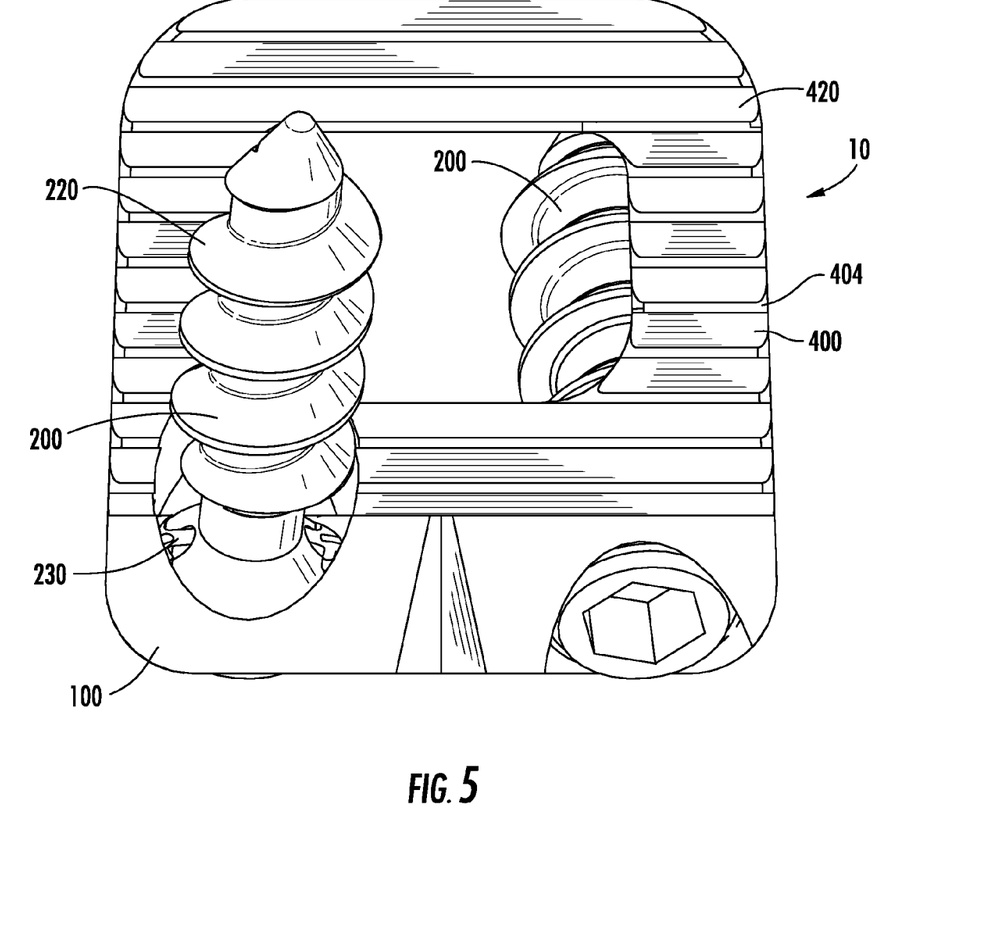
FIG. 5 is a top plan view of one aspect of the spinal fusion system of FIG. 1.

As shown in FIG. 1, the fastener 200 can comprise a bone screw. It is contemplated that the fastener can also comprise a pin, staple, or other fastening means. In another aspect, to prevent the fastener from backing out of the fastener bore, the system comprises means for retaining the at least one fastener 200 in the at least one fastener bore. Where the fastener comprises a bone screw, the bone screw can comprise a head 210 and a threaded shank 220. In an exemplified aspect, a portion of the shank 220 defines a retaining bore 222 therethrough, through which a flexible retainer pin 230 may be positioned. In this aspect, the retainer pin has a length L greater than at least a portion of a diameter $D_1$ of the fastener bore 110 such that at least a portion of the flexible retainer pin juts out from at least one of the ends of the retaining bore. The flexible retaining pin is configured to bias toward the head 210 of the screw during insertion into fastener bore, making its effective length less than the diameter $D_1$ of the fastener bore, and bias back to substantially an original position after insertion, thereby retaining the bone screw within the fastener bore. In yet another aspect, the flexible retainer pin 230 comprises a distal cross member 236 positioned at least adjacent its distal end 237 and a proximal cross member 234 positioned at least adjacent its proximal end 233 for retaining the retainer pin 230 within the retaining bore. As one skilled in the art can appreciate, the system can function with various prior art screw retaining mechanisms, as well.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A spinal fusion system for positioning between a first and second vertebral body, the system comprising:
a rigid titanium body having a longitudinal axis and a first modulus of elasticity, and a posterior face, the rigid body defining at least one fastener bore therethrough, each bore configured for receipt of at least one fastener, wherein each fastener comprises a bone screw having a head and a threaded shank and is configured for insertion into a vertebral body;
a rigid titanium plate integral to a portion of the posterior face of the rigid body, extending away from and transverse to the posterior face of the rigid body, the rigid plate defines a plurality of cavities therethrough; and
a first thermoplastic implant body and a second thermoplastic implant body wherein the first implant body and the second implant body each have a first inner and a second outer surface and wherein the first implant body and the second implant body connect at their respective first surfaces, the first surfaces having a plurality of projections, and within each of the cavities are matingly connected at their first respective surfaces by the plurality of projections of the first implant body interlocking with the plurality of projections of the second implant body, each body having a modulus of elasticity less than or equal to the first modulus of elasticity, wherein the first and second implant bodies are configured to matingly connect to one another with the rigid plate positioned therebetween, and wherein the combination of the first and second implant bodies and the rigid plate is configured for insertion between the first and second vertebral bodies, and
further comprising a flexible retainer pin for retaining one of the at least one bone screw in a respective fastener bore, the flexible retainer pin positioned through a retaining bore in a portion of the head of the bone screw, wherein a portion of the flexible retainer pin juts out from at least one end of a wall defined by the retaining bore, and wherein the flexible retaining pin is configured to bias toward the head of the bone screw during insertion of the bone screw into the fastener bore, making its effective length less than the diameter of the fastener bore, and bias back to an original position after insertion, thereby retaining the bone screw within the fastener bore.

2. The spinal fusion system of claim 1, wherein the rigid plate is bisected by a first plane and wherein the longitudinal axis is contained in the first plane.

3. The spinal fusion system of claim 2, wherein the at least one fastener bore comprises a plurality of fastener bores, and wherein the at least one bone screw comprises a first and second bone screw, the first bone screw being angled upwardly with respect to the first plane and the second bone screw being angled downwardly with respect to the first plane.

4. The spinal fusion system of claim 3, wherein the first and second Bone screws are oppositely disposed at equal angles.

5. The spinal fusion system of claim 4, wherein the equal angles are between 20 degrees and 45 degrees.

6. The spinal fusion system of claim 5, wherein the equal angles are 35 degrees.

7. The spinal fusion system of claim 1 wherein the thermoplastic material comprises polyetheretherketone.

8. The spinal fusion system of claim 1, wherein at least one of the second surfaces of the first implant body and the second implant body are ramped downwardly away from the rigid body.

9. The spinal fusion system of claim 8, wherein at least one of the second surface of the first implant body and the second implant body define ridges.

10. The spinal fusion system of claim 1, wherein the flexible retainer pin comprises a distal cross member positioned adjacent to its distal end and a proximal cross member positioned adjacent to its proximal end for retaining the flexible retainer pin within the retaining bore.

11. The spinal fusion system of claim 1, wherein the first implant body has a first thickness and the second implant body has a second thickness.

12. The spinal fusion system of claim 11, wherein the first thickness is equal to the second thickness.

13. A spinal fusion system for positioning between a first and second vertebral body, the system comprising: a rigid titanium body having a longitudinal axis and a posterior face, the rigid body defining at least one fastener bore therethrough, each bore configured for receipt of at least one bone screw, wherein each bone screw has a head and a threaded shank and is configured for insertion into one of the first or second vertebral bodies; a rigid plate integrally connected to a portion of the posterior face of the rigid body, extending away from and transverse to the posterior face of the rigid body, the rigid plate defines a plurality of cavities therethrough; and a first thermoplastic implant body and a second thermoplastic implant body wherein the first implant body and the second implant body each have a first and a second surface and wherein the first implant body and the second implant body connect at their respective first surfaces, the first surfaces having a plurality of projections, and within each of the cavities are matingly connected at their first respective surfaces by the plurality of projections of the first implant body interlocking with the plurality of projections of the second implant body, each implant body comprising a thermoplastic material, wherein the first and second implant bodies are configured to matingly connect to one another with the rigid plate positioned therebetween, and wherein the combination of the first and second implant bodies and the rigid plate is configured for insertion between the first and second vertebral bodies, and further comprising a flexible retainer pin for retaining one of the at least one bone screw in a respective fastener bore, the flexible retainer pin positioned through a retaining bore in a portion of the head of the bone screw, wherein a portion of the flexible retainer pin juts out from at least one end of a wall defined by the retaining bore, and wherein the flexible retaining pin is configured to bias toward the head of the bone screw during insertion of the bone screw into the fastener bore, making its effective length less than the diameter of the fastener bore, and bias back to an original position after insertion, thereby retaining the bone screw within the fastener bore.

14. The spinal fusion system of claim 13, wherein the rigid plate is bisected by a first plane and wherein the longitudinal axis is contained in the first plane.

15. The spinal fusion system of claim 14, wherein the at least one fastener bore comprises a plurality of fastener bores, and wherein the at least one bone screw comprises a first and second bone screw, the first bone screw being angled upwardly with respect to the first plane and the second bone screw being angled downwardly with respect to the first plane.

16. The spinal fusion system of claim 15, wherein the first and second bone screws are oppositely disposed at equal angles.

17. The spinal fusion system of claim 16, wherein the equal angles are between 20 degrees and 45 degrees.

18. The spinal fusion system of claim 17, wherein the equal angles are 35degrees.

19. The spinal fusion system of claim 13, wherein the thermoplastic material comprises polyetheretherketone.

20. The spinal fusion system of claim 13, wherein the first implant body has a first thickness and the second implant body has a second thickness.

21. The spinal fusion system of claim 20, wherein the first thickness is equal to the second thickness.

* * * * *